United States Patent
Steuer et al.

(10) Patent No.: US 7,455,816 B2
(45) Date of Patent: Nov. 25, 2008

(54) SUPPORT PLATE FOR CARRYING OUT FUNCTIONAL TESTS ON BIOLOGICAL CELLS AND METHOD FOR COATING THE SUPPORT PLATE

(75) Inventors: Heiko Steuer, Pfullingen (DE); Markus Templin, Tuebingen (DE); Britta Kanzok, Tuebingen (DE); Cornelia Kuschel, Moessingen (DE); Brigitte Angres, Pfullingen (DE)

(73) Assignee: NMI Naturwissenschaftliches und Medizinisches Institut an der Universitaet Tuebingen, Reutlingen (DE)

( * ) Notice: Subject to any disclaimer, the term of this patent is extended or adjusted under 35 U.S.C. 154(b) by 162 days.

(21) Appl. No.: 11/704,525

(22) Filed: Feb. 9, 2007

(65) Prior Publication Data
US 2007/0218546 A1    Sep. 20, 2007

Related U.S. Application Data

(63) Continuation of application No. PCT/EP2005/007334, filed on Jul. 7, 2005.

(30) Foreign Application Priority Data
Aug. 10, 2004    (DE) .................. 10 2004 039 628

(51) Int. Cl.
*B01L 3/00* (2006.01)
(52) U.S. Cl. .............................. 422/102; 435/4; 435/7.1; 435/7.9; 435/6; 436/180; 436/524; 422/68.1; 422/82.01; 427/2.11; 427/561; 427/97.1; 427/121

(58) Field of Classification Search ................ 435/4, 435/5, 7.1, 7.9; 436/180, 524; 422/68.1, 422/82.01, 102; 427/2.11, 561, 97.1, 121
See application file for complete search history.

(56) References Cited

U.S. PATENT DOCUMENTS

| 5,208,111 | A | 5/1993 | Decher et al. |
| 6,548,263 | B1 | 4/2003 | Kapur et al. |
| 2002/0019018 | A1 | 2/2002 | Christopherson et al. |
| 2003/0129296 | A1 | 7/2003 | Kelso |
| 2004/0081979 | A1 | 4/2004 | Knezevic et al. |

FOREIGN PATENT DOCUMENTS

| EP | 0 366 241 | 5/1990 |
| EP | 1 162 459 | 12/2001 |
| EP | 1 535 952 | 6/2005 |

(Continued)

OTHER PUBLICATIONS

International Search Report for PCT/EP2005/007334, mailed on Nov. 21, 2005, 3 pages.

(Continued)

*Primary Examiner*—Jill Warden
*Assistant Examiner*—Jyoti Nagpaul
(74) *Attorney, Agent, or Firm*—Morrison & Foerster LLP

(57) ABSTRACT

The invention relates to a method for coating a support plate for carrying out functional tests on biological cells, to a support plate for carrying out functional tests on biological cells and to the use of corresponding support plates for carrying out functional tests on biological cells.

18 Claims, 2 Drawing Sheets

FOREIGN PATENT DOCUMENTS

| | | |
|---|---|---|
| WO | WO-95/25116 | 9/1995 |
| WO | WO-02/02226 | 1/2002 |
| WO | WO-02/085423 | 10/2002 |

OTHER PUBLICATIONS

Mandenius et al., Analytical Letters (1989) 22(15):2961-2973.
Tonkinson and Stillman, Frontiers in Bioscience (2002) 7:1-12.
International Preliminary Report on Patentability for PCT/EP2005/007334, mailed Apr. 12, 2007, 4 pages.

SUPPORT PLATE FOR CARRYING OUT FUNCTIONAL TESTS ON BIOLOGICAL CELLS AND METHOD FOR COATING THE SUPPORT PLATE

CROSS-REFERENCES TO RELATED APPLICATION

This application is a continuation of copending international patent application PCT/EP/2005/007334 filed on Jul. 7, 2005 and designating the U.S., which was not published under PCT Article 21(2) in English, and claims priority of German patent application DE 10 2004 039 628.0 filed on Aug. 10, 2004, all of which are incorporated herein by reference.

BACKGROUND OF THE INVENTION

1. Field of the Invention

The invention relates to a method for coating a support plate for carrying out functional tests on biological cells, to a support plate for carrying out functional tests on biological cells and to the use of corresponding support plates for carrying out functional tests on biological cells.

In the field of fundamental biological research and in applied biotechnology, for example drug screening or diagnosis, support plates for example of glass or plastic are used, by means of which a multiplicity of studies such as interactions between biological material and chemical/biological substances can be studied. To this end the support plates are generally coated, for example with poly-L-lysin, via which biological material such as biological cells is fixed onto the surface of the support plate. Functional tests can then be carried out on the fixed cells. Support plates configured in such a way are also referred to as biochips. The coating of the support plate with a very wide variety of materials is of crucial importance, since all subsequent steps such as the application of biomolecules, colonization with biological cells and the reproducibility of the functional tests by means of the finished biochip depend thereon.

2. Prior Art

WO 02/02226 A2, which is incorporated herein by reference, discloses a method for coating a support plate, in which polylysin is spotted onto an aldehyde-activated surface of the support plate by means of conventional inkjet technology or contact printing methods. In a subsequent step, extracellular matrix (ECM) proteins are bound covalently to the previously activated polylysin. In order to avoid non-specific binding of cells to the aldehyde-activated surface, aldehyde groups still free inside and above all outside the microspots are saturated. The same treatment is also carried out whenever proteins are bound directly to aldehyde-activated surfaces. The disadvantage of the method is that the saturation of the aldehyde groups is not sufficient to fully prevent non-specific binding of cells.

U.S. Pat. No. 6,548,263 B1, which is incorporated herein by reference, discloses a method which attempts to prevent such non-specific binding of cells on regions outside the microspots loaded with biomolecules. A support plate made of glass, plastic or silicone is chemically modified in this case, for example with aminosilane (3-aminopropyltrimethoxysilane). Proteins which are spotted onto this surface can be bound to the reactive groups of the aminosilane either directly or via hetero-bifunctional groups. Before the binding of the biomolecules takes place, cell-repellent hydrophobic coating is carried out in regions outside the microspots in order to prevent non-specific binding of cells to these reactive groups. The method disclosed here is an elaborate multistage method. A further disadvantage of the method described in U.S. Pat. No. 6,548,263 is that the same site is doubly spotted congruently, which is very difficult in practice since reaching the same microspots requires utmost precision of the equipment, which is not available with most arrayers.

US 2002/0019018 A1, which is incorporated herein by reference, discloses a nitrocellulose-coated support plate in the form of a glass slide, monoclonal antibodies being fixed onto the support plate via the nitrocellulose. Details about the coating method are not disclosed.

Glass carriers which have a nitrocellulose surface are furthermore available on the market. This surface can be saturated by corresponding reagents, in order to avoid non-specific adhesion to cells. The nitrocellulose layer, however, has the disadvantage that biological material to be fixed thereon, for example ECM (extracellular matrix) proteins, is absorbed in a sponge-like fashion owing to the high suction ability of the compact nitrocellulose layer, thereby lost deep in the layer and no longer available for subsequent colonization with biological cells. The adhesion of the cells is relatively weak, even though large amounts of the ECM proteins are cost-intensively used. In order to generate a protein layer which is effective for the cell adhesion and accessible to the cells, unnecessarily high concentrations of proteins must be applied, which is difficult with microarrayers, especially inkjet arrayers.

SUMMARY OF THE INVENTION

It is therefore an object of the present invention to provide a method for coating a support plate, with which the disadvantages of the prior art are avoided. In particular, it is intended to permit coating which allows reliable and high-quality fixing of biomaterial, which furthermore enables simple saturation of non-specific adhesion sites for cells outside the biomolecule spots and which ensures good adhesion with or of biological cells via bound biomolecules.

This object is achieved on the one hand by a method as mentioned in the introduction, which comprises the following steps:

(a) providing a support plate with a first layer, which comprises at least one hydrogen bridge donor and/or at least one polycation, and (b) coating the support plate, coated with the first layer, with a hydrogen bridge acceptor and/or a polyanion, in particular nitrocellulose or derivatives thereof.

This object of the invention is hereby fully achieved. In fact, the inventors have discovered that nitrocellulose in particular can be applied after prior coating of the support plate with a layer comprising a polycation. This ensures good adhesion of the nitrocellulose and provides a substrate for the application of biomolecules, for example components of the extracellular matrix, which can be colonized in a further step with the biological cells to be studied. The support plate produced in this way combines the good properties of a nitrocellulose-coated support plate, i.e. simple saturation of non-specific binding sites, as well as simple production of the support plate.

In this context "support plate" is intended to mean any device similar to a plate or platelet which is suitable for being used to carry out functional tests on biological cells, for example glass plates, plastic plates, in particular plastic plates made of polystyrene and/or silicone, etc. in the form of multiwell plates.

According to one aspect in step (a), a support plate is provided with a layer which comprises a substance that is selected from poly-L-lysin, poly-D-lysin, polyimide, aminosilane or derivatives thereof.

In the method according to the invention, coating with poly-L-lysin has been found to be particularly suitable.

Furthermore, for example, instead of a nitrocellulose layer it is also possible to apply a layer which comprises a substance that is selected from the group comprising cellulose, DEAE-cellulose, polysulfone or derivatives thereof or combinations of said substances.

It is furthermore preferable for the coating in step (b) to be carried out so that a thin and rough or smooth nitrocellulose layer is formed.

The thin layer of nitrocellulose ensures that the diffusion space which is traveled by the solution is kept small. In contrast to thick or compact nitrocellulose layers, in which the spreading of the biomolecules—and therefore also the diameter of the biomolecule spot on the carrier surface—depends on the reagent solution, the carrier according to the invention can therefore also be used for quantitative cell determinations. The carriers according to the invention can furthermore be used in transmitted light microscopy, since in them—in contrast to carriers with thicker nitrocellulose layers—the light is not scattered in this layer and a diffuse image is not therefore created. In this type of microscopy, cells can therefore be observed simply and reliably on the carrier according to the invention.

In this context "thin" is intended to mean any layer thickness which still allows microscopy with transmitted light with the support plates thus formed, but which at least is less than approximately 15,000 nm.

In this context "rough" is intended to mean any layer whose surface does not have a uniform appearance—in contrast to the surface of the "smooth layer". Overall, therefore, the rough layer comprises a larger surface than a comparable smooth layer.

According to one aspect, the coating in step (b) is carried out by applying a methanol-nitrocellulose solution and subsequently evaporating the methanol.

According to another aspect of the method according to the invention, the methanol-nitrocellulose solution is applied by spraying the support plate.

Both methods have the advantage that, after the methanol has evaporated, a rough nitrocellulose layer is formed in a straightforward way. The nitrocellulose layer thereby formed has a substantially rough surface.

This provides a larger surface than in the case of smooth nitrocellulose layers or only chemically activated surfaces. In a further step, therefore, more biomaterial e.g. extracellular matrix proteins can be applied or immobilized, and a better substrate can thus be provided for colonization with biological cells since comparatively more biomolecules per unit area are thereby available to bind biological cells.

As an alternative, the methanol-nitrocellulose solution is applied by immersing the support plate in the solution.

After the immersion, the support plate is removed and dried in air. This method has the advantage that a relatively smooth nitrocellulose layer can thereby be formed.

Said coating measures have the advantage that extremely thin nitrocellulose layers can be formed with a layer thickness of approximately 100 to approximately 1200 nm. This avoids a sponge effect by which the biomaterial is absorbed into the lower layers of the nitrocellulose layer and thereby lost, so that the majority of the biomaterial is available for binding to cells.

For a multiplicity of functional tests, the biomaterial is applied in the form of drops onto the support plate. In this context, it is particularly advantageous to form thin nitrocellulose layers since the diameter of the resulting so-called microspots can be controlled well owing to the short diffusion paths of the biomaterial lying in solution. The term "microspots" is accordingly intended to mean point-like spreading of the biomaterial on the support plate surface. In functional tests in which cell counts per microspot are determined, more reliable and better-reproducible results are therefore achieved.

The support plate is in this case sprayed by means of conventional techniques, for example by using a compressed-air gun (airbrush gun) or nebulizing the methanol-nitrocellulose solution over the support plate coated with a polycation layer using corresponding equipment. According to the alternative procedure, the carrier coated with a polycation layer is immersed in a vessel which contains methanol-nitrocellulose solution.

According to a variant according to the invention, in step (a0) an uncoated support plate is coated with a layer which comprises a substance that is selected from the group comprising poly-L-lysin, poly-D-lysin, polyimide, aminosilane or derivatives thereof.

This measure has the advantage that a multiplicity of commercially available support plates can be used, which are not yet pre-coated with a layer that comprises at least one hydrogen bridge donor and/or at least one polycation. The user of the method according to the invention therefore has even greater freedom in selecting the appropriate support plate, so that for example microtiter plates may also be used.

According to another aspect of the invention, a furthermore step (c) is carried out in which biomolecules are applied or immobilized onto the coated support plate.

The term biomolecules is intended to mean any biological substances such as proteins, carbohydrates, lipids etc. In particular, so-called capture molecules such as antibodies, cell surface proteins, receptors, ligands, lectins, antigens and allergens etc. may be envisaged.

According to the invention, it is preferable for the biomolecules to be selected from the group consisting of: proteins, in particular proteins of the extracellular matrix such as fibronectin, laminin, thrombospondin, collagen, elastin, tenascin, vitronectin; carbohydrates, in particular carbohydrates of the extracellular matrix such as glycosaminoglycans; proteoglycans; lipids.

With the support plates fabricated in this way, for example, it is possible for binding tests to be carried out i.e. tests which, for example, study what cell types or how many cells have bound to the respective biomolecules.

Applying components of the extracellular matrix onto the support plate coated with for example a first polycation layer and with nitrocellulose provides a substantially natural environment for the cells, so that the original biological functional status of these cells can be sustained. For instance, it is known that the extracellular matrix co-controls cell functions and differentiations. This measure thus provides an in vivo-like situation in vitro and therefore a higher likelihood of rapidly finding in vivo active substances, for example in drug screening. Conversely, merely plastic surfaces are used for cell colonization in most cell-based screening assays, which often leads to dedifferentiation and the loss of cell functions.

According to another aspect of the invention, a further step (c') is carried out in the method according to the invention, in which test substances are applied onto the coated support plate. The test substances are preferably selected from the group consisting of: pharmaceutical preparations; antibodies; substances which influence the properties of biological cells; messengers; growth factors; antigens; allergens.

By bringing cells to be immobilized in contact with said test substances, the cells can be deliberately stimulated or generally influenced in their properties, i.e. the potential of such a test substance for influencing the biological cells can be studied. Equally, for example when antibodies directed against tumor markers are being used as a test substance, a support plate which can be used for cancer cell screening is provided.

In an exemplary embodiment the biomolecules and/or test substances are applied by means of contactless printing or by means of contact-mediated printing.

The contactless printing can be carried out by means of inkjet technology, or via piezoelectric printing, and for the contact-mediated printing to be carried out by the pin-and-ring method or the split-pin method.

Methods for carrying out inkjet technology are disclosed for example in the US patent specifications numbered U.S. Pat. Nos. 5,233,369 and 5,486,855 the contents of which are incorporated herein by reference. A general overview of methods for contact-mediated printing as well as for contactless printing is found for example in "Microarray Biochip Technology", Schena, M, Ed., 2000.

For example, contactless printing ensures that uniform amounts of the biomolecules or test substances are always applied, and that no dispersion of this material takes place. Conversely, in conventional so-called contact printing with a dot matrix printer, there is a large variation in the amounts of material applied from application to application. The problem of protein dispersion when creating microspots is also often observed. These disadvantages, however, are avoided by the preferred measures.

In an exemplary embodiment of the method according to the invention, the biomolecules and/or test substances are prepared in a printing buffer which contains trehalose in a final concentration of from 0.1 to 5% (w/v), preferably 0.5% (w/v), and NP 40 in a final concentration of from 0.00001 to 0.1% (v/v), preferably from 0.0003 to 0.005% (v/v).

This, however, does not exclude other commercially available printing buffers from being usable, for example the "Protein Printing Buffer Arraylt"™ printing buffer from Telechem, USA.

As the inventors have found, using such a printing buffer in the scope of piezoelectric printing ensures the formation of regular patterns or regular microspots and substantially avoids the creation of so-called undesired satellite spots or irregular patterns. The functional tests to be carried out therefore give more reliable and reproducible results.

According to another embodiment of the method according to the invention, a further step (d) is carried out in which the pre-treated support plate is incubated with a protein solution, preferably a 5 vol. % (w/v) strength BSA-PBS solution. Here, it is nevertheless also possible to use other so-called block buffers, for example the commercially available block buffer "StabilGuard" from SurModics.

This measure has the advantage that non-specific binding sites in the biomaterial-coated microspot, for example the extracellular matrix proteins, and non-specific cell binding sites of the nitrocellulose outside the microspots on the carrier are saturated. The preferred concentration of BSA (bovine serum albumin) in PBS (phosphate-buffered saline) has been found to be one which ensures optimal saturation of such binding sites.

According to another aspect a further step (e) is carried out in the method according to the invention, in which biological cells are applied onto the pre-treated support plate.

Further tests can be carried out with such prefabricated support plates. After adding soluble substances, for example, it is possible to study how and to what substances the cells fixed on the support plate react.

According to get another aspect the support plate prepared in step (a) is made of a material which is selected from the group consisting of: glass; plastic, in particular polystyrene and/or silicone.

With this measure, it is advantageous that the functional tests to be carried out can be evaluated microscopically, particularly in the scope of transmitted light measurements, in which case poly-L-lysin and nitrocellulose-coated surfaces, on which the biomaterial and/or test substances can be readily applied and/or immobilized, may preferably be provided on glass and plastic.

The present invention furthermore relates to a support plate for carrying out functional tests on biological cells, consisting of a base plate which is coated with a first layer that comprises at least one hydrogen bridge donor and/or at least one polycation, and a layer of a hydrogen bridge acceptor and/or a polyanion, in particular nitrocellulose or derivatives thereof, applied thereon. In particular, it is preferable for the first layer to comprise a substance that is selected from the group comprising poly-L-lysin, poly-D-lysin, polyimide, aminosilane or derivatives thereof.

In these plates, it is advantageous that the first polycation layer ensures good adhesion of the nitrocellulose.

Instead of the nitrocellulose layer, it is for example also possible to use a layer which comprises cellulose, DEAE-cellulose, polysulfone or derivatives thereof.

A thin layer of nitrocellulose, and in particular a nitrocellulose layer with a layer thickness of from approximately 100 to approximately 1200 nm, is preferably provided in the support plate according to the invention.

This ensures that the aforementioned sponge effect is substantially avoided.

Depending on the method of applying the nitrocellulose layer, the surface is either smooth or rough. Particularly in the latter case, a large surface is provided for the biomaterial to be applied, for example extracellular matrix proteins, because of the roughness.

According to another aspect in the test plate, a layer of biomolecules and/or test substances is applied onto the nitrocellulose layer, the biomolecules preferably being selected from proteins, in particular proteins of the extracellular matrix such as fibronectin, laminin, thrombospondin, collagen, elastin, tenascin, vitronectin; carbohydrates, in particular carbohydrates of the extracellular matrix such as glycosaminoglycans; proteoglycans; lipids. The test substances are preferably selected from pharmaceutical preparations; antibodies; substances which influence the properties of biological cells; messengers; growth factors; antigens; allergens.

By these measures when ECM components are selected, a support plate is provided which offers a substantially natural in vivo-like environment for the cells to be immobilized, so that dedifferentiation of cells and artifact measurements can be avoided in the scope of the functional tests. Furthermore, when capture molecules or pharmaceutical preparations are selected, a support plate is provided which can be used for cancer cell screening or even for stimulating cells, and which therefore represents an important instrument for diagnosis and drug screening.

According to a preferred refinement, biological cells are applied onto the biomolecules and/or test substances.

This provides an already test-ready support plate in the form of a biochip for direct use.

According to another aspect, the base plate of the support plate according to the invention is made of a material which is selected from the group consisting of: glass; plastic, in particular polystyrene and/or silicone.

This measure has the advantage that on the one hand a coated surface can be provided advantageously by means of standard methods and, on the other hand, the evaluation of the functional tests by means of microscopic transmitted light measurements is also made possible.

The present invention furthermore relates to the use of the support plate described above, or the support plate produced by the method described above, for carrying out functional tests on biological cells.

It is to be understood that the features mentioned above and those yet to be explained below may be used not only in the combination respectively indicated, but also in other combinations or in isolation, without departing from the scope of the present invention.

The present invention will now be explained in more detail with the aid of exemplary embodiments and figures, from which further advantages and properties will be found.

DETAILED DESCRIPTION

EXAMPLE 1

Coating the Support Plate with Nitrocellulose

Figure 1:
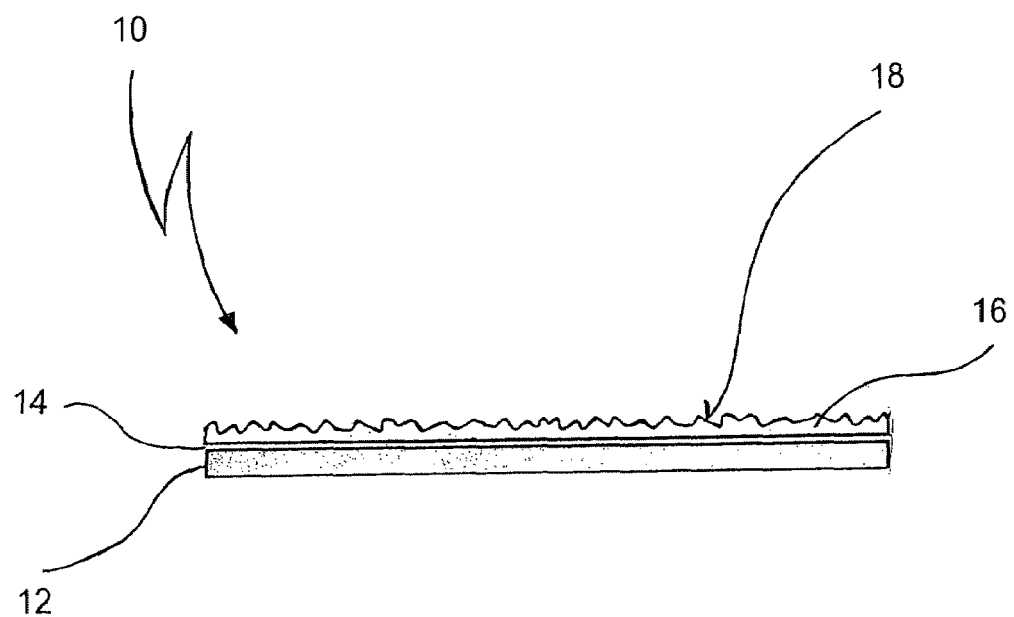
FIG. 1 shows an embodiment of the support plate according to the invention.

Slides already coated with poly-L-lysin (Poly-Prep-Slides, sigma P0425) were used as support plates. The coating with nitrocellulose solution can be carried out in two ways:

(A) Coating by the Spray Method

The slides were placed vertically next to one another lengthwise on a rail. The nitrocellulose solution (2.5 mg/ml methanol) was applied onto them by an airbrush gun, which was guided slowly along at a distance of 18 cm parallel to the slides. The spraying was repeated fourteen times, the methanol evaporating within a short time after each spray process.

(B) Coating by the Immersion Method

The slides were clamped vertically suspended by the writing surface from a rail. With the aid of a corresponding motor-driven device, the slides were lowered into a vessel holding the nitrocellulose solution (20 mg/ml methanol). After 10 min, the slides were removed slowly (10 cm/min) from the solution and dried by suspending for 10 min. In order to check the uniformity of the nitrocellulose layer, the slides coated as described were scanned with high amplification (for example gain 90) for example by means of a GMS 418 arrayer scanner. Non-uniformly coated slides were rejected and not used.

EXAMPLE 2

Coating the Support Plate with Biomolecules

The following steps were carried out sterilely, or in a clean room.

For coating a support plate pre-treated according to Example 1 with biomolecules (here as an example: ECM molecules), two different printing buffers were needed: buffer I (0.5% (w/v) trehalose with 0.05% (v/v) NP40 in PBS: for all ECM proteins described in Example 5 except for collagens) and buffer 11 (0.5% (w/v) trehalose with 0.0003% (v/v) NP40 in PBS: for collagens). BSA-Tamra (bovine serum albumin, which has been covalently coupled to the fluorescent dye carboxytetramethylrhodamine) was added to the printing buffers in a final concentration of 1 µg/ml. Adding the BSA-Tamra to the biomolecule solution made it possible for the protein solution to be made visible via a laser scanner after application onto the support plate, and therefore for the correctness of the microspot pattern to be checked directly after printing. After washing the slide with saturation solution (see Example 3) the BSA-Tamra, which was adsorbed onto the carrier surface like the other biomolecules in the printing buffer, was used for relative quantification of the protein adsorbed onto the support plate. The printing buffers were used doubly concentrated, and mixed 1:2 with the biomolecules, which were present in double concentration of the desired final concentration in PBS. The ECM molecules mixed with printing buffer were centrifuged for 15 min at 4° C. at 15000 g (for example Eppendorf centrifuge 5810R with a rotor for Eppendorf tubes: 12000 rpm) and pipetted into a plate with 384 wells (Genetix X6003; 20 to 40 µl per well). The plate was centrifuged again for 10 min at 4° C. at 1500 g (for example Hettich centrifuge with a rotor for multiwell plates, 4000 rpm).

The slides were coated or printed with the biomolecules using the BioChipArrayer (Packard) according to the manufacturer's instructions (for example an array with 8×8 microspots, 12 arrays per slide). It was important here to comply with the washing procedures of the BioChip arrayer as specified by the manufacturer.

In order to verify correct coating of the support plate with the biomolecules, the slides were scanned at low amplification (for example gain 30). The microspots appear in the linear range with the false colors blue or green. Both the printing pattern and the relative amounts of the protein spotted per microspot can thus be verified indirectly through quantifying the fluorescence of the added BSA-Tamra. After scanning, the slides were stored at 4° C. in closed containers.

EXAMPLE 3

Saturating Non-Specific Binding Sites of the Support Plate

The following steps were carried out sterilely, or in a clean room.

After storage for approximately 2 days (or longer, see below), the slides prepared according to Examples 1 and 2 were acclimatized for one hour at room temperature, "blocked" with StabilGuard (SurModics SG01B04) or BSA solution (BSA from Roth T844; 5% (w/v) in PBS; heat-inactivated for 1 h at 50° C.) and dried at room temperature. The "blocking", i.e. saturation of the non-specific binding sites, can be carried out in various ways:

(A) Saturating Non-Specific Binding Sites with the aid of a Spray Method

Here, the slides lying horizontally were wetted with a spray mist until they were covered uniformly with a moisture film. The spray bottle was held vertically at approximately 30 cm in front of the slides. After one hour at room temperature, the slides were dried for 30 min with the printed side pointing obliquely downward.

(B) Saturating Non-Specific Binding Sites by the Immersion Method

Here, the slides were immersed with the writing field upward in a cuvette of block solution, removed after one hour and dried for 30 min with the printed side pointing obliquely downward. They were subsequently stored at 4° C. in closed containers.

In order to check the relative amounts of adsorbed ECM proteins in the microspots, the blocked slides were scanned and the intensities of the fluorescence of the microspots, caused by BSA-Tamra added to the spotted ECM protein solution, were determined by a quantification program (for example Imagene, BioDiscovery).

As an alternative to this, after a storage time longer than just 2 days, the slides may be blocked not until immediately before the colonization with biological cells. In this case the unblocked stored slides are acclimatized for 1 h at room temperature and blocked optionally in one of two different ways directly before the colonization:

(C) Blocking by the Immersion Method

The slides were immersed with the writing field upwards in a cuvette of block solution, removed after one hour, immersed once in PBS solution and provided while wet with a Pro-Plate culture module (Grace BioLabs, USA). The cavities were immediately filled with 200 µl of PBS each.

(D) Blocking in the Culture Module

The unblocked slides were provided with a Pro-Plate culture module (Grace BioLabs, USA). The cavities were each filled with 200 µl of block solution and incubated for 30 min at room temperature. The cavities were washed twice with PBS solution and colonized with biological cells (cf. below).

When blocking according to methods (C) and (D), drying and scanning were omitted and colonization of the support plate with the biological cells (Example 4) followed directly.

EXAMPLE 4

Colonization of the Support Plate with Biological Cells (A) General Guidelines:

The number of cells to be used depends on the intended incubation time and the type of assay which is to be carried out after the colonization. The cell count per microspot should lie in the linear range, i.e. in the sub-confluent range, and was optimized in preliminary experiments. The cells were distributed over the slide by shaking it.

The shaking has two functions: 1st Ensuring a uniform distribution of the cells within the cavities. The slides must be shaken immediately after seeding the cells, before the cells have settled on the bottom of the cavities. 2nd Concentrating the cells on the microspots. Cells which have not sunk onto microspots, or which have not adhered, are returned into the supernatant by the shaking and again have the opportunity to adhere on a permissive substrate.

The success of the adhesion of cells on microspots depends on the shear forces generated and therefore the strength and duration of the shaking, and the time intervals between shaking processes. In order to obtain meaningful results in the test, the strength, duration and frequency of the shaking are therefore adapted to the cell adhesion forces of the cell type being used and the nature of the assay, and accordingly optimized in preliminary experiments.

All the pipetting steps are carried out by hand with the aid of a Pasteur pipette and a pipetting ball or micropipettes. When removing the liquid from a cavity, the bottom must remain fully covered with liquid; the cavities must immediately be refilled individually after removing the liquid. Colonized microspots should not become dry until the cells are fixed.

(B) Regarding the Conduct:

All the following steps were carried out sterilely, or in a clean room.

The support plates or slides produced according to Examples 1 to 3 were colonized by means of ProPlate culture modules: a silicone seal and a plastic culture module were placed onto the slides acclimatized at room temperature for 1 h and fixed by lateral rails.

The cavities were washed three times for 5 min with PBS and each filled with 200 µl of a cell suspension (for example 1.5 times 105 cells/ml). Directly after the seeding and during the further culture in the breeding cabinet for 2 h, the slides were shaken on a Variomag microtiter plate shaker (H+P Labortechnik, Teleshake 4, order No 51440) at intervals of 10 min (shaking mode circularly counterclockwise, 4 s, 750 x/min).

The culture modules were removed, the slides were individually immersed once in 50 ml Falcon tubes in PBS solution containing calcium and magnesium ions; adhering cells were subsequently dyed in 50 ml Falcon tubes, for example with Coomassie Brilliant Blue dye solution (0.05% w/v Coomassie Brilliant Blue, 50 vol. % methanol, 10 vol. % glacial acetic acid, 40 vol. % $H_2O$) for 10 min at room temperature.

The slides were immersed three times in PBS and subsequently overcoated with DAPI solution while lying (Sigma; 0.5 µg/ml in PBS; 5 min at room temperature) and again immersed in PBS. The slides were briefly dried while placed vertically on absorbent paper and embedded with Mowiol or ProLong (Molecular Probes P-7481).

The adhered cells were photographed by means of photobinoculars or, for quantitative analysis, by a fluorescence microscope with a motor stage and quantified with the aid of Leica Qwin macros produced therefore.

EXAMPLE 5

Differential Adhesion of Three Cell Lines on Microspots Comprising Different Extracellular Proteins In a further experiment, support plates pre-coated with poly-L-lysin and nitrocellulose were coated according to Example 2 with microspots respectively comprising different ECM proteins as the biomolecule: BSA, collagen type I, collagen type II, collagen type III, collagen type V, laminin EHS, fibronectin, laminin hupl (human placenta), thrombospondin, heparan sulfate proteoglycan, vitronectin, tenascin, collagen type IV hupl, collagen type IV EHS, fibronectin rec (recombinantly produced fibronectin, EMP Genetech, Denzlingen).

FIG. 1 schematically represents a support plate coated according to the invention.

In FIG. 1, a coated support plate is denoted overall by 10. A first layer 14, for example a polycation layer of poly-L-lysin, is applied onto a glass slide 12. The first layer 14 is coated with a second layer 16 that comprises for example nitrocellulose, which has a rough surface 18. Owing to the roughness of the surface 18, the overall surface of the second layer 16 is increased relative to a comparable smooth layer. It is therefore possible to apply more biomaterial onto the support plate 10 then would be the case with a smooth surface. Depending on the use of the support plate 10, a smooth surface of the second layer 16 may nevertheless be suitable, for example whenever the amount of biomaterial to be applied need not or should not be so great as in the case of a second layer 16 provided with a rough surface.

The biomolecules were each printed into four microspots as an array of 64 microspots in all. There were a total of 12 arrays on the entire slide. These arrays were separated into 12 cavities with the aid of the culture module, and could thus be seeded with biological cells independently of one another. 20,000 cells were seeded per cavity in order to carry out the assay.

In parallel batches, the microspots were respectively seeded with the cell lines HEK 293, NIH 3T3 and PC 12, cultured for 2 h while shaking, fixed and dyed with DAPI. The number of cells on the microspots was subsequently determined. The result of such an experiment is represented in FIGS. 2A and 2B.

Figure 2A:
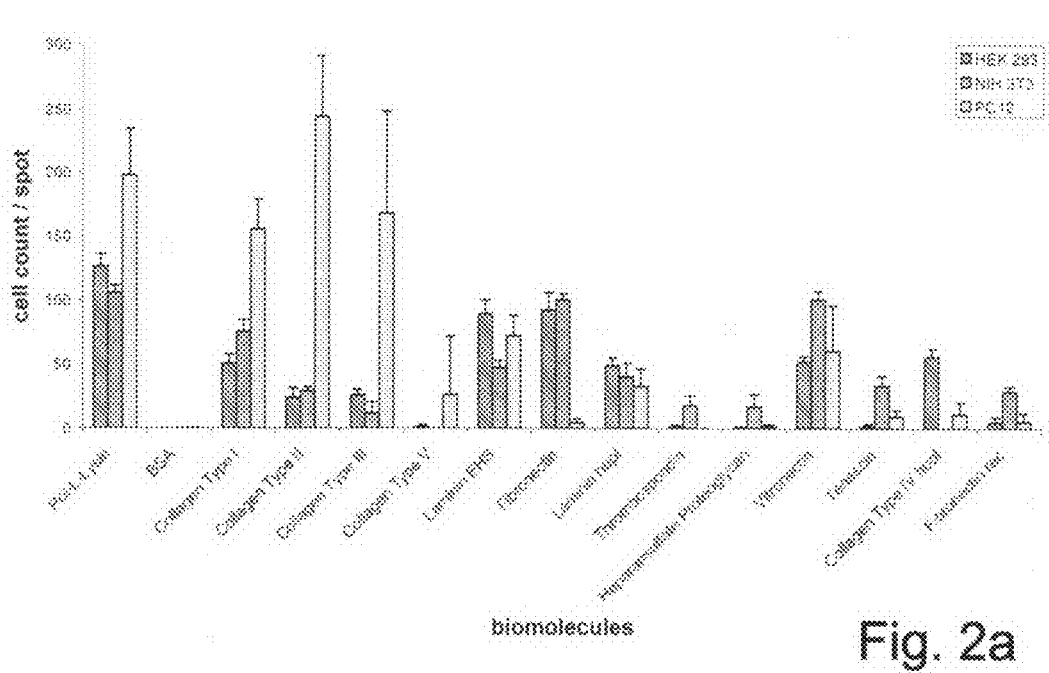
FIG. 2 shows the differential adhesion of three cell lines onto support plates coated with different ECM proteins [(A) absolute cell counts; (B) relative cell counts].

The average values of the number of bound cells of the cell lines HEK 293 (respectively left-hand bar), NIH 3T3 (respectively middle bar) and PC 12 (respectively right-hand bar) are plotted in FIG. 2A, each case on four microspots of the same biomolecule.

Figure 2B:
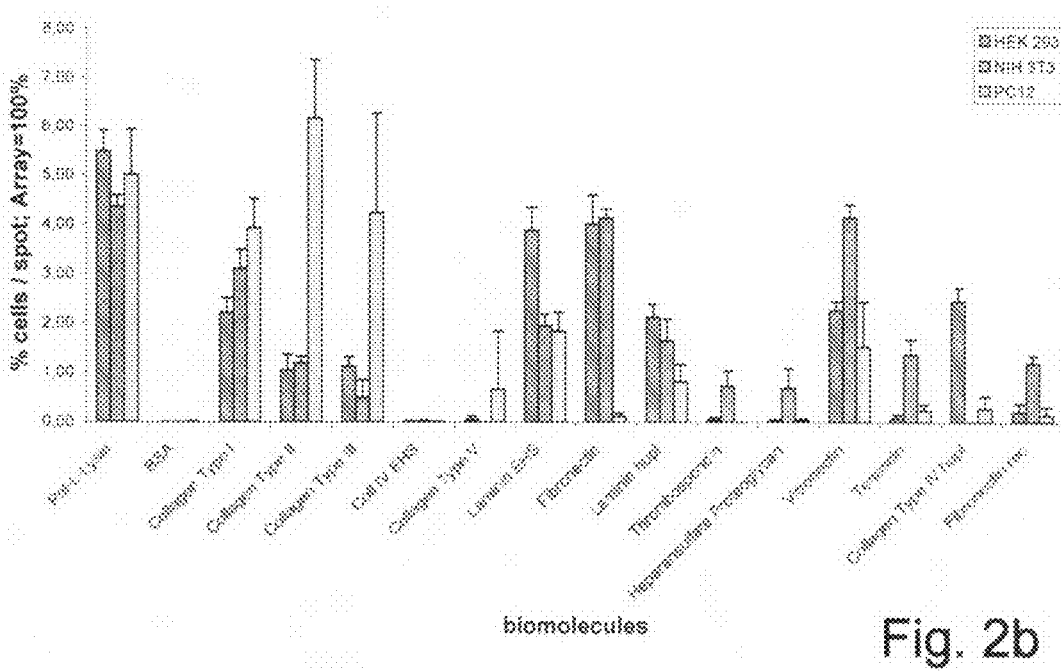

FIG. 2B similarly represents the percentage proportion of the number of bound cells, normalization of the cell count having been carried out so that the total number of cells on an array corresponds to 100%.

It can be seen in that different colonization densities were achieved for various ECM proteins depending on the cell line type. The support plate coated according to the invention can therefore be coated successfully with extracellular matrix proteins. Depending on the extracellular matrix protein, these can in turn be colonized with different cell lines and give a characteristic pattern for each cell lines, by which their affinity for the respective protein is replicated.

Therefore, what is claimed is:

1. A method for coating a support plate for carrying out functional tests on biological cells, which method comprises the following steps:
   (a) providing a support plate with a first layer, which comprises poly-L-lysin or derivatives thereof, and
   (b) coating the support plate, coated with the first layer, with nitrocellulose or derivatives thereof, such, that a rough nitrocellulose-layer with a layer thickness of approximately 100 to approximately 1200 nm is formed.

2. The method for coating a support plate as claimed in claim 1, wherein the coating in step (b) is carried out by applying a methanol-nitrocellulose solution and subsequently evaporating the methanol.

3. The method for coating a support plate as claimed in claim 1, wherein the coating in step (b) is carried out by spraying the support plate with a methanol-nitrocellulose solution and subsequently evaporating the methanol.

4. The method for coating a support plate as claimed in claim 1, wherein the coating in step (b) is carried out by immersing the support plate in a methanol-nitrocellulose solution and subsequently evaporating the methanol.

5. A method for coating a support plate as claimed in claim 1, which method comprises the additional step:
   (c) applying biomolecules onto the coated support plate.

6. The method for coating a support plate as claimed in claim 1, which method comprises the additional step:
   (c) applying biomolecules onto the coated support plate, which biomolecules are selected from proteins, in particular proteins of the extracellular matrix such as fibronectin, laminin, thrombospondin, collagen, elastin, tenascin, vitronectin; carbohydrates, in particular carbohydrates of the extracellular matrix such as glycosaminoglycans; proteoglycans; lipids.

7. A method for coating a support plate as claimed in claim 1, which method comprises the additional steps:
   (c) applying biomolecules onto the coated support plate, and
   (d) applying test substances onto the coated support plate.

8. The method for coating a support plate as claimed in claim 1, which method comprises the additional steps:
   (c) applying biomolecules onto the coated support plate, and
   (d) applying test substances onto the coated support plate, which test substances are selected from pharmaceutical preparations; antibodies; substances which influence the properties of biological cells; messengers; growth factors; antigens; allergens.

9. A method for coating a support plate as claimed in claim 1, which method comprises the additional steps:
   (c) applying biomolecules onto the coated support plate, and
   (d) incubating the pre-treated support plate under a protein solution.

10. A method for coating a support plate as claimed in claim 1, which method comprises the additional steps:
    (c) applying biomolecules onto the coated support plate,
    (d) incubating the pre-treated support plate under a protein solution, and
    (e) applying biological cells onto the pre-treated support plate.

11. The method for coating a support plate as claimed in claim 1, wherein the support plate prepared in step (a) is made of one or two of glass, plastics, polystyrene, silicone.

12. A support plate for carrying out functional tests on biological cells, consisting of a base plate which is coated with a first layer that comprises poly-L-lysin or derivatives thereof and a second nitrocellulose layer having a layer thickness of approximately 100 to approximately 1200 nm.

13. The support plate as claimed in claim 12, wherein a layer of biomolecules is applied onto the nitrocellulose layer.

14. The support plate as claimed in claim 12, wherein a layer of test substances is applied onto the nitrocellulose layer.

15. The support plate as claimed in claim 12, wherein a layer of biomolecules is applied onto the nitrocellulose layer, the biomolecules being selected from proteins, proteins of the extracellular matrix, fibronectin, laminin, thrombospondin, collagen, elastin, tenascin, vitronectin; carbohydrates, lipids.

16. The support plate as claimed in claim 12, wherein a layer of test substances is applied onto the nitrocellulose layer, the test substances being selected from pharmaceutical preparations; antibodies; substances which influence the properties of biological cells; messengers; growth factors; antigens; allergens.

17. The support plate as claimed in claim 12, wherein the base plate is made of one or two of glass; plastics, polystyrene and/or silicone.

18. A method for coating a support plate for carrying out functional tests on biological cells, which method comprises the following steps:
    (a) providing a support plate with a first layer, which comprises at least one hydrogen bridge donor or at least one polycation, and
    (b) coating the support plate, coated with the first layer, with nitrocellulose of derivatives thereof.

* * * * *